United States Patent [19]

Gadebusch et al.

[11] Patent Number: 4,782,059

[45] Date of Patent: Nov. 1, 1988

[54] METHOD OF CONTROLLING MYCOTIC INFECTIONS AND COMPOSITIONS THEREFOR

[75] Inventors: Hans H. Gadebusch, Yardley, Pa.; Mary E. Valiant, Plainfield, N.J.

[73] Assignee: Merck & Co., Inc., Rahway, N.J.

[21] Appl. No.: 913,044

[22] Filed: Sep. 29, 1986

[51] Int. Cl.[4] .................. A61K 31/50; A61K 31/495; A61K 31/135
[52] U.S. Cl. ..................................... 514/252; 514/657
[58] Field of Search ............................... 514/252, 657

[56] References Cited

PUBLICATIONS

Sud et al., Antimicrobial Agents and Chemotherapy, 28, pp. 532–534 (1985).
Fromtling, Drugs of Today, 20 pp. 325–349 (1984).

Primary Examiner—Jerome D. Goldberg
Attorney, Agent, or Firm—Alice O. Robertson; Michael C. Sudol

[57] ABSTRACT

Certain fungistats when employed in combination have been found to exhibit synergistic antifungal properties and further exhibit fungicidal properties.

7 Claims, 2 Drawing Sheets

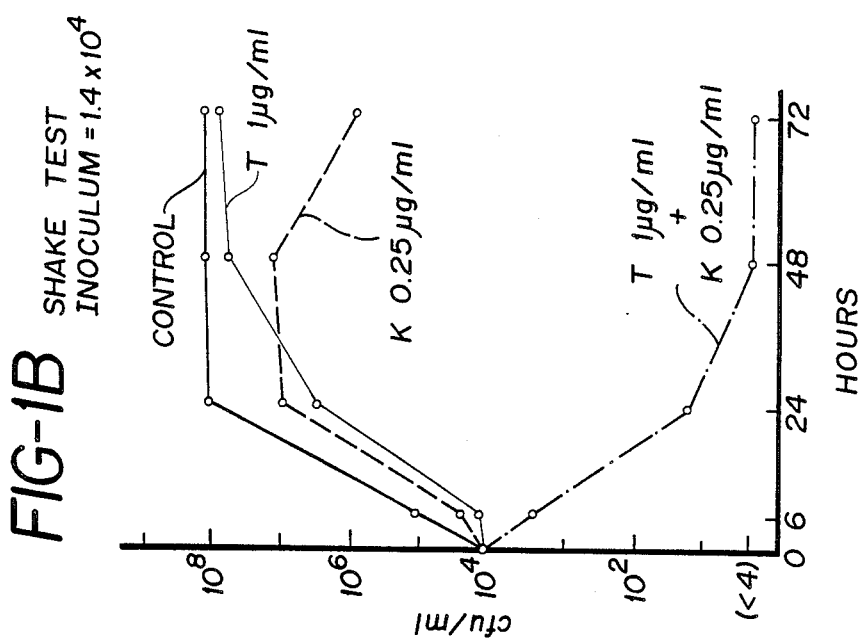
FIG-1B SHAKE TEST INOCULUM = 1.4 × 10⁴
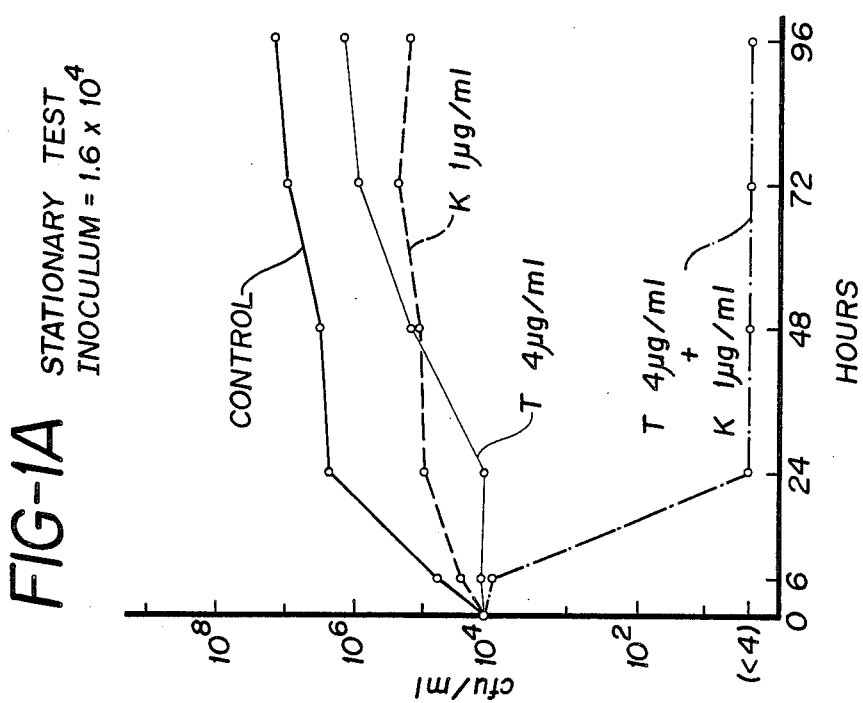
FIG-1A STATIONARY TEST INOCULUM = 1.6 × 10⁴

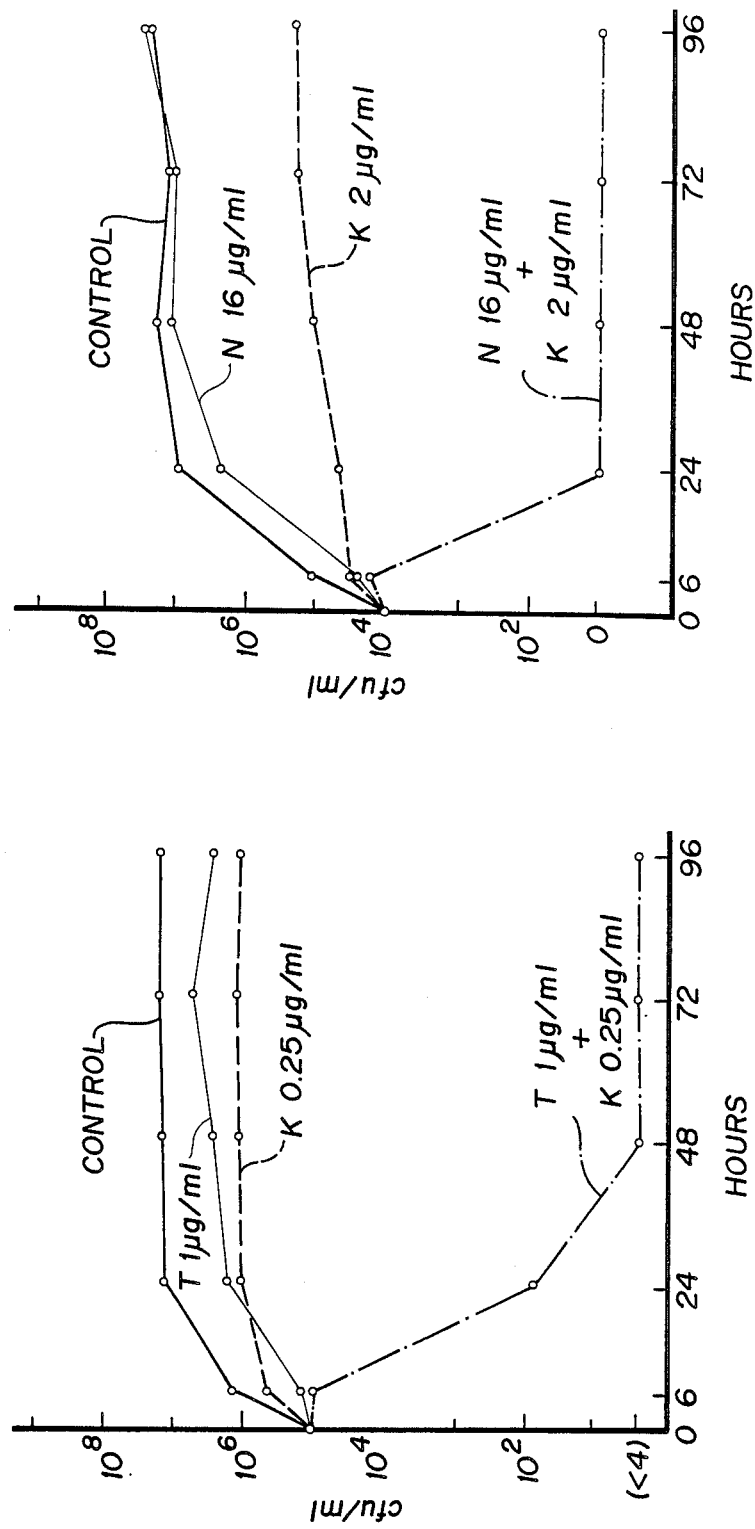

METHOD OF CONTROLLING MYCOTIC INFECTIONS AND COMPOSITIONS THEREFOR

BACKGROUND OF THE INVENTION

Antigungal agents considered with specific reference to systemic fungal infections caused by organisms such as Candida species, *Cryotococcus neoformans, Histoplasma capsulatum* and the like, are found for the most part to be fungistatic, i.e., merely inhibit the growth of the fungal organism without effecting a kill. A few fungicidal agents are known. Amphotericin B and other polyenes are known to damage membranes that contain ergosterol and therefore are effectively fungicidal. However, their use is normally precluded because of a number of severe side effects. Other possibly fungicidal drugs have side effects or as in the case of 5-fluorocytosine is limited by the scope of its spectrum. 5-Fluorocytosine is further limited by the ease with which an organism develops resistance to it. In the search for useful antifungal drugs it is desirable to find a drug or a combination of drugs which is effective at low levels thereby minimizing side effects. It is particularly desirable to find a drug or a combination of drugs in which the drug is fungicidal.

STATEMENT OF THE INVENTION

The present invention concerns an improved method for the treatment of human mycotic infections made possible by the discovery that when certain fungistatic agents known to be inhibitors in fungal sterol synthesis are employed in combination, a synergistic antifungal combination is obtained. It has further been found that the combination not only inhibits the growth of fungi to an extent much greater than that which would result from an additive effect of the components but that such amounts are able to cause irreversible damage to the fungi resulting in a killing or cidal effect on the fungi. The invention also concerns compositions which are suitable for use in the treatment of mycotic infections.

DESCRIPTION OF THE INVENTION

The fungistats which in combination have been found to produce this unexpected synergistic and fungicidal effect have been found to belong to a class of compounds which are known to be inhibitors of 14α-methyldemethylase and inhibitors of squalene epoxidase. By using a combination of compounds from compounds having these properties there is provided a method for treating human mycotic infections.

The process of the present invention comprises treating subjects with mycotic infections by directing to the site where control is desired a therapeutically effective antifungal amount of a composition comprising (1) a compound which has a 14α-methylase inhibitor property and (2) a compound which has a squalene epoxidase inhibitor property. By "directing to the site where control is desired" is meant that the application may be made at a site remote from that of the infection such as would be the case with oral or parenteral administration. The agents may be administered simultaneously or sequentially and either agent may be administered first. They may be administered with or without a pharmaceutically acceptable carrier in the amounts hereinafter set forth. By the administration of the amounts of the agents as hereinafter set forth, a synergistic interaction and further a fungicidal effect of the drugs is achieved which is wholly unexpected. The preferred method of administration may vary with the site where control is desired. One preferred method of administration is by the use of pharmaceutical compositions in unit dosage form as described below which provides a convenient simultaneous administration method.

The compounds which have 14α-methyldemethylase inhibitor activity which are essential as one component of the antifungal compositions to be employed in treating human mycotic infections preferably are azoles, especially imidazoles and triazoles. Many of these compounds are in use clinically as fungistats or are being developed for such purpose. The generic drug names for those compounds already developed or being developed have the suffix "conazole". In subsequent discussions, the compounds will sometimes be referred to as "conazole compounds", even though some may not have a generic name. The foremost compound is ketoconazole which is cis-1-acetyl-4-[4-[[2-(2,4-dichlorophenyl)-2(1H-imidazol-1-ylmethyl)-1,3-dioxolan-4-yl]methoxy]phenyl]piperazine. Other fungistatic conazole compounds which are 14α-methyldemethylase inhibitors and which are either in clinical use or in development include miconazole, 1-[2,4-dichloro-β-(2,4-dichlorobenzyloxy)phenethyl]imidazole as nitrate; econazole, 1-[2-(2,4-dichlorophenyl)-2-(4-chlorobenzyloxy)ethyl]imidazole; isoconazole, 1-[2,4-dichloro-β-(2,6-dichlorobenzyloxy)phenethyl]imidazole as nitrate; terconazole, cis-1[4-[[2-(2,4-dichlorophenyl)-2-(1H-1,2,4-triazol-1-ylmethyl)-1,3-dioxolan-4-yl]methoxyl]phenyl]-4-(1-methyphenyl)-piperazine; tioconazole, 1-[2-[(2-chloro-3-thienyl)methoxy]-2-(2,4-dichlorophenyl)ethyl]-1H-imidazole; bifonazole, 1-](4-biphenyl)phenylmethyl]1H-imidazole. Still other azoles include ICI-153066 (ICI Pharmaceutical Division), [(R,S)-1-(2,4-dichlorophenyl)-1-(4-fluorophenyl)-2-(1,2,4-triazol-1-yl)ethanol]; Bay-n-7133 (Bayer AG, West Germany), 1-(4-chlorophenoxy)-3,3'-dimethyl-2-(1,2,4-triazo-1-yl)-methyl(E)-1-(5-chlorothien-2-yl)-2-(2H-imidazol-1-yl)ethanone-2,6-dichlorophenylhydrazone hydrochloride; SM-4470 (Sumitomo Chemical Co., Ltd.), (R)-3-(n-butylthio)-2-(2,4-dichlorophenyl)-1-(imidazol-1-yl)-2-propanol hydrochloride; oriconazole or itraconazole, (+)-cis-4-[4-[4-[[2-(2,4-dichlorophenyl)-2-(1H-1,2,4-triazol-1-ylemethyl)-1,3-dioxolan-4-yl] methoxy]phenyl]-1-piperazinyl]phenyl]-2,4-dihydro-2-(1-methylpropyl)-3H-1,2,4-triazol-3-one; fenticonazole, α-(2,4-dichlorophenyl)-β,N-imidazolylethyl-4-phenylthiobenzylether nitrate; oxiconazole, (Z)-[(2,4-dichloro-2-imidazol-1-yl)acetophenone]-0-(2,4-dichlorobenzyl)oxime; [2-(p-omoconazole (E)-1-[2,4cloro-β-[2chlorophenoxy)ethoxy]-α-methylstyryl-]imidazole; aliconazole. Still other imidazole antifungal compounds which may be employed include 1-methyl-4-[3-(2-methyl-5-nitro-1H-imidazol-1-yl)propyl]piperazine, 5-nitro-(1-methylimidazolyl-t-butyl)(2-hydroxy-5-methoxyphenyl)carbinol, Z-1-[2-(2,4-dichlorophenyl)-3-methyl-1-pentenyl]-1H-imidazole hydrochloride, cis-3-(2-chloro-3-thienylmethyloxy)-2,3-dihydro-5-fluoro-2-(1-imidazoylmethyl)benzo[b]thiophene.

The compounds may have a basic nitrogen ard therefore may be present as an acid addition salt. Reference to conazole compounds is intended to embrace both forms.

The squalene epoxidase inhibitors which are useful in the present invention are allylamine compounds, specifically terbinafine, (E)-N-(6,6-dimethyl-2-hepten-4-ynyl)-N-methyl-1-naphthalenemethylamine; and naftifine, N-methyl-N-(3-phenyl-2-propenyl)-1-naphthalenemethanamine hydrochloride.

Many of the conazole compounds are established antifungal compounds. With the greater efficacy and further, fungicidal properties made possible by its use in combination with naftifine or terbinafine or other squalene epoxidase inhibitors, their potential in the control of mycotic infections is greatly enhanced. Ketoconazole is one of the preferred antifungal compounds for its broad spectrum and very little side effects. The combination of ketoconazole and naftifine or terbinafine represent preferred embodiments of the present invention.

The synergistic antifungal and fungicidal combinations of the present invention are effective in the treatment of mycotic infections caused by such fungal organisms as Candida species, for example, *C. albicans, C. parapsilosis, C. tropicalis, C. pseudotropicalis, C. Krusei, C. rugosa, C. quilliermondii. C. stellatoidea;* Aspergillus species such as *A. fumigatus; Cryptococcus neoformans; Torulopsis galbrata; Rhizapus rhizopodiformis; Coccidioides immitis; Sporothrix schenkii; Histoplasma capsulatum;* and *Blastomyces dermatitidis.*

The efficacy of the combination of the present invention in producing a synergistic antifungal as well as a fungicidal effect may be seen in the in vitro interaction studies for the determination of activity and determination of viable cells. In these tests against representative fungal organisms known to be the causative agent of mycotic infections, synergistic antifungal properties have been demonstrated with ketoconazole and naftifine and with ketoconazole and terbinafine against numerous strains of *Candida albicans,* other Candida species as well as a number of other fungal organisms. Representative antifungal properties of the combination ketoconazole-naftifine and the combination ketoconazole-terbinafine have been demonstrated against *Candida albicans.* many) supplemented with 0.5 percent glycerol to aliquots of the diluted samples. Nine parts of agar were employed for each part of solution containing drug or a mixture of drugs. Where mixtures of drug was to be tested, the solution containing the drugs were mixed immediately prior to the addition of agar.

Yeast fungal cultures which had been maintained on Sabouraud's dextrose agar were transferred to yeast maltose broth and incubated at 35° C. with shaking at 250 rpm for 24 hours. Appropriate dilutions were made with 0.85 percent saline to obtain final concentrations of fungi of approximately $1 \times 10^6$ cfu/ml (colony forming units per milliliter).

The drug-agar plates were inoculated with fungal cultures using a Denley Multipoint Inoculator which delivers approximately 0.001 milliliter to the agar surface resulting in inocula of $1 \times 10^3$ cfu. The plates were then incubated at 28° C. for 48 hours, read, and the minimum inhibitory concentrations (MIC) recorded. MIC was taken as the lowest concentration showing no growth or less than 3 cfu/spot.

Determination of the existence of synergism was made following procedure in "Antibiotics in Laboratory Medicine", by Victor Lorian, William and Wilkens, 1980, pp 300–304. Drug combinations were considered to be synergistic when the "FIC index" (fractional inhibitory concentration index) was found to be ≦0.5. The fractional inhibitory concentration (FIC) for each drug was determined by dividing the minimum inhibitory concentration (MIC) of the drug when in combination by the MIC of the drug when tested alone. The FIC index is the summation of the two values. An FIC index of >0.5 but <2.0 is considered to be an additive effective and ≧2.0 to indicate antagonism.

The results of combinations showing synergistic effect are seen in Table I.

TABLE I

| | Minimum Inhibitory Concentration mg/ml | | | |
|---|---|---|---|---|
| Fungal Organism | Terbinafine (T) | Ketoconazole (K) | Combination (T:K)* | FIC Index |
| Candida albicans MY1055+ | 128.0 (32)++ | 32.0 | 4:0.25, 2:0.25, 1:0.25 | 0.05–0.13 (3)** |
| C. albicans MY992 | >128.0 (256) | 8.0 | 64:2 | 0.5 or less (1) |
| C. albicans MY1013 | 128.0 (64) | 16.0 | 32:0.25, 16:0.25, 8:0.25, 4:0.25, 2:0.25, 0.5:0.25 | 0.02–0.26 (6) |
| C. albicans MY1029 | >128.0 (16) | 32.0 | 4:0.125, 2:0.125, 0.5:8 | 0.13–0.28 (3) |
| C. albicans MY1058 | >128.0 (128) | 0.5 | 64:0.25 | 1.0 |
| C. tropicalis MY1011 | >128.0 (128) | 128.0 | 32:0.5, 16:0.5, 4:1 | 0.04–0.25 (3) |
| C. tropicalis MY1012 | 4.0 (4) | 128.0 | 2:4 | 0.53 |
| C. krusei MY1020 | >128.0 (64) | 4.0 | 16:1, 8:1 | 0.38–0.5 (2) |
| C. guilliermondie MY1019 | 8.0 (8) | 2.0 | 2:0.5, 1:0.5 | 0.38–0.5 (2) |
| Cryptococcus neoforman MY1050 | 1.0 (1) | 8.0 | 0.125:2, 0.25:2 | 0.38–0.5 (2) |
| Cr. neoforman MY1051 | 0.5 (0.5) | 1.0 | 0.25:0.5 | 1.0 |
| Torulopsis glabrata MY1059 | >128.0 (256) | 8.0 | 64:2, 32:2, 16:2 | 0.31–0.5 or less (3) |
| Saccharomyces cerevisiae MY1027 | 16.0 (16) | 16.0 | 4:2, 2:4 | 0.38 (2) |

*The minimum inhibitory concentration of the combination (terbinafine:ketoconazole) giving a FIC index in the range indicated
**Number of combinations indicated by number in parenthesis
+Internal identification of strain of organism
++The figure in parenthesis is the number used in calculating the FIC index. The number indicates the concentration at which it was noted that growth was reduced even though the extent of reduced growth was not sufficient to designate it as inhibitory concentration

KETOCONAZOLE AND TERBINAFINE

A. Synergistic Effect

Terbinafine and ketoconazole were separately dissolved in dimethylsulfoxide (DMSO) and diluted with water to obtain a concentration of drug of 1.28 milligrams/milliliter in 10 percent DMSO. Subsequent serial twofold dilutions were made with water.

Drug-agar plates were then prepared by adding molten Kimmig's agar (E. Merck, Darmstadt, W. Germany)

B. Fungicidal Effect

Terbinafine and ketoconazole solutions were prepared as described in Part A except that DMF was used as the initial solvent, and 10 percent DMF in water was used for subsequent dilutions.

Drug-culture tubes containing one part drug or mixtures of drugs were prepared by combining one part drug solution with nine parts of broth (Kimmig's medium) previously seeded with *C. albicans* MY1013.

Each tube including yeast culture control tube contained 1% DMF. The yeast culture employed for seeding was that restored from Sabouraud's dextrose agar slant and grown in broth for 24 hours as previously described and containing about $10^8$ cfu/ml. The broth was thereafter diluted first 1:10 or 1:100 with 0.85% saline and then 1:100 with Kimmig's medium to obtain the broth composition which when added to the drug culture tubes provided culture concentrations therein of approximately $10^4$ and of $10^5$ cfu/ml.

The inoculated tubes were incubated at 35° C. in some cases with shaking and in other cases without shaking, and aliquots were removed at 6 hours and further at 24, 48, 72 and 96 hours as indicated. The aliquots were diluted in saline and plated in Sabouraud's dextrose agar. The plates were incubated at 35° C. for at least 48 hours and the colonies then counted. From the counts obtained, the number of cfu/ml in the undiluted drug-culture tubes was calculated.

B-1 Initial inoculum of $1.6 \times 10^4$ cfu/ml and incubation without shaking

In the first test, the effect of drug, mixture of drugs and no drug on growth of *Candida albicans* initially inoculated at $1.6 \times 10^4$ cfu/ml was determined. The concentration of drugs employed were for terbinafine, 1.0, 4.0, 16.0 and 64.0 μg/ml; for ketoconazole, 1.0, 4.0 and 16.0 μg/ml; for the mixture, 1.0 terbinafine:4.0 ketoconazole and 4.0 terbinafine:1.0 ketoconazole. The incubation has carried out under stationery conditions and readings made at 0, 6, 24, 48, 72 and 96 hours.

The results are seen on Table II. The results show that (1) in unmedicated control tubes, there is a fourfold increase in growth in 6 hours, a 2 log increase in 24 hours, and a maximum density of $1-2 \times 10^7$ cfu/ml in 72 hours; (2) in terbinafine containing tubes, at concentrations of 16 μg/ml or less, there was at best only a fungistatic effect during the 96 hour test period; (3) in the ketoconazole containing tubes, at concentrations of 1 μg/ml and 4 μg/ml, the effect was less than fungistatic although the maximum growth attained was lower than that of the control, and at a concentration of 16 μg/ml, the effect was fungistatic at 24 hours and slowly fungicidal during the next 72 hours. The lowest concentration for the combinations (a) terbinafine 1 μg/ml and ketoconazole 4 μg/ml and (b) terbinafine 4 μg/ml and ketoconazole 1 μg/ml were fungistatic for the first 6 hour period and fungicidal by 24 hours. Fungicidal effects were also obtained employing drug combinations at higher concentrations.

TABLE II

Stationery Test
Inoculum $1.6 \times 10^4$ cfu/ml

| | mg/ml | 0 hrs | 6 hrs | 24 hrs | 48 hrs | 72 hrs | 96 hrs |
|---|---|---|---|---|---|---|---|
| | | cfu/ml[a] | | | | | |
| Control | $0^b$ | $1.6 \times 10^4$ | $7.8 \times 10^4$ | $4.3 \times 10^6$ | $5.4 \times 10^6$ | $1.4 \times 10^7$ | $1.8 \times 10^7$ |
| Terbinafine | 1.0 | $1.6 \times 10^4$ | $2.7 \times 10^4$ | $3.0 \times 10^6$ | $8.2 \times 10^6$ | $1.3 \times 10^7$ | $1.1 \times 10^7$ |
| | 4.0 | $1.6 \times 10^4$ | $2.4 \times 10^4$ | $2.1 \times 10^4$ | $2.5 \times 10^5$ | $1.0 \times 10^6$ | $2.4 \times 10^6$ |
| | 16.0 | $1.6 \times 10^4$ | $3.2 \times 10^4$ | $1.3 \times 10^4$ | $5.4 \times 10^4$ | $4.3 \times 10^4$ | $1.0 \times 10^6$ |
| | 64.0 | $1.6 \times 10^4$ | $3.8 \times 10^4$ | $6.9 \times 10^4$ | $3.2 \times 10^2$ | $3.3 \times 10^3$ | $1.4 \times 10^4$ |
| Ketoconazole | 1.0 | $1.6 \times 10^4$ | $5.3 \times 10^4$ | $1.1 \times 10^5$ | $1.5 \times 10^5$ | $4.1 \times 10^5$ | $3.2 \times 10^5$ |
| | 4.0 | $1.6 \times 10^4$ | $3.3 \times 10^4$ | $8.8 \times 10^4$ | $7.0 \times 10^5$ | $1.9 \times 10^5$ | $1.0 \times 10^5$ |
| | 16.0 | $1.6 \times 10^4$ | $3.7 \times 10^4$ | $1.1 \times 10^4$ | $2.5 \times 10^3$ | $2.9 \times 10^2$ | $<4^c$ |
| Turbinafine + Ketoconazole | 1.0 4.0 | $1.6 \times 10^4$ | $1.2 \times 10^4$ | $<4^c$ | $<4^c$ | $<4^c$ | $<4^c$ |
| Turbinafine + Ketoconazole | 4.0 | $1.6 \times 10^4$ | $1.7 \times 10^4$ | $<4^c$ | $<4^c$ | $<4^c$ | $<4^c$ |

[a]Determined after dilution with saline and plating on Sabouraud's dextrose agar.
[b]Control tube and all drug-culture tubes contained a final concentration of 1% DMF, the solvent for the test agents.
[c]<4 cfu/ml = lower limit of the assay.

FIG. 1A compares growth in the presence of terbinafine (T) alone at a concentration of 4 μg/milliliter ketoconazole (K) alone at a concentration of 4 μg/milliliter of combination of drugs at a concentration of 4 μg/ml of ketoconazole and 1 μg/ml of terbinafine and clearly shows the fungicidal effect of the combination.

B-2 Initial Inoculum of $1.4 \times 10^4$ cfu/ml and incubation while shaking

In another test, the effects of drug, mixture of drugs and no drug on the growth of *Candida albicans* from an initial fungal inoculum concentration of $1.4 \times 10^4$ cfu/ml under conditions where the shaking is employed were compared.

The results are seen in Table III.

The table shows that when a combination of drugs are employed, either (i) terbinafine at 0.25 μg/ml plus ketoconazole at 1 μg/ml or (ii) terbinafine at 1 μg/ml and ketoconazole at 0.25 μg/m, the fungicidal effect was complete in 48 hours and a marked fungicidal effect was noted in 24 hours. The effect of the latter combination and a comparison thereof with the effect of terbinafine at 1 μg/ml and ketoconazole at 0.25 μg/ml are seen in FIG. 1B. When the combination concentrations were increased to (i) terbinafine at 1 μg/ml plus ketoconazole at 4 μg/ml or (ii) terbinafine at 4 μg/ml plus ketoconazole at 0.25 μg/ml, a completely fungicidal effect was obtained by 24 hours.

TABLE III

Shake Test
Inoculum $1.4 \times 10^4$ cfu/ml

| | mg/ml | 0 hrs | 6 hrs | 24 hrs | 48 hrs | 72 hrs |
|---|---|---|---|---|---|---|
| | | cfu/ml[a] | | | | |
| Control | $0^b$ | $1.4 \times 10^4$ | $1.5 \times 10^5$ | $1.1 \times 10^8$ | $1.7 \times 10^8$ | $1.7 \times 10^8$ |
| Terbinifine (T) | 0.25 | $1.4 \times 10^4$ | $3.2 \times 10^4$ | $8.6 \times 10^7$ | $1.1 \times 10^8$ | $1.4 \times 10^8$ |
| | 1.0 | $1.4 \times 10^4$ | $2.6 \times 10^4$ | $6.0 \times 10^6$ | $8.5 \times 10^7$ | $1.2 \times 10^8$ |
| | 4.0 | $1.4 \times 10^4$ | $1.3 \times 10^4$ | $7.6 \times 10^3$ | $8.6 \times 10^4$ | $2.6 \times 10^7$ |
| | 16.0 | $1.4 \times 10^4$ | $1.7 \times 10^4$ | $2.0 \times 10^3$ | $2.2 \times 10^3$ | $1.1 \times 10^6$ |

TABLE III-continued

| | | Shake Test Inoculum $1.4 \times 10^4$ cfu/ml cfu/ml[a] | | | | |
|---|---|---|---|---|---|---|
| | mg/ml | 0 hrs | 6 hrs | 24 hrs | 48 hrs | 72 hrs |
| Ketoconazole (K) | 0.25 | $1.4 \times 10^4$ | $5.4 \times 10^4$ | $1.2 \times 10^7$ | $1.8 \times 10^7$ | $9.7 \times 10^6$ |
| | 1.0 | $1.4 \times 10^4$ | $6.6 \times 10^4$ | $1.1 \times 10^7$ | $1.5 \times 10^7$ | $1.8 \times 10^6$ |
| | 4.0 | $1.4 \times 10^4$ | $3.8 \times 10^4$ | $4.0 \times 10^5$ | $1.2 \times 10^7$ | $8.0 \times 10^5$ |
| | 16.0 | $1.4 \times 10^4$ | $2.1 \times 10^4$ | $5.4 \times 10^3$ | $5.0 \times 10^3$ | $3.6 \times 10^3$ |
| (T) 0.062 + (K) | 4.0 | $1.4 \times 10^4$ | $1.9 \times 10^4$ | $3.4 \times 10^4$ | $6.6 \times 10^5$ | $9.1 \times 10^5$ |
| (T) 0.25 + (K) | 1.0 | $1.4 \times 10^4$ | $9.1 \times 10^3$ | $4.8 \times 10^2$ | $<4^c$ | $<4^c$ |
| (T) 0.25 + (K) | 4.0 | $1.4 \times 10^4$ | $1.1 \times 10^4$ | $7.3 \times 10^1$ | $<4^c$ | $<4^c$ |
| (T) 1.0 + (K) | 0.25 | $1.4 \times 10^4$ | $4.8 \times 10^3$ | $2.5 \times 10^1$ | $<4^c$ | $<4^c$ |
| (T) 1.0 + (K) | 1.0 | $1.4 \times 10^4$ | $6.4 \times 10^3$ | $1.2 \times 10^1$ | $<4^c$ | $<4^c$ |
| (T) 1.0 + (K) | 4.0 | $1.4 \times 10^4$ | $4.8 \times 10^3$ | $<4^c$ | $<4^c$ | $<4^c$ |
| (T) 4.0 + (K) | 0.25 | $1.4 \times 10^4$ | $7.9 \times 10^3$ | $<4^c$ | $<4^c$ | $<4^c$ |

[a]Determined after dilution with saline and plating on Sabouraud's dextrose agar.
[b]Control tube and all drug-culture tubes contained a final concentration of 1% DMF, the solvent for the test agents.
[c]<4 cfu/ml = lower limit of the assay.

B-3 Initial inoculum of $1.1 \times 10^5$ and incubation without shaking

In still another test, the effect on a higher initial fungal inoculum of $1.1 \times 10^5$ cfu/ml was determined under conditions where media were stationery during incubation. The results are seen in Table IV.

The results show that when terbinafine was employed alone at 4 μg/ml, only fungistatic control was obtained. At higher levels of 16 μg/ml and 64 μg/ml, there was seen a reduction in viability of <1 log during the 24-48 hour period and then a gradual increase in growth. Ketoconazole when employed alone at 64 μg/ml was slowly fungicidal but when the concentration was 16 μg/ml or lower, the effect was only slightly fungistatic. The combinations of (i) terbinafine at 0.062 μg/ml, plus ketoconazole at 16 μg/ml, (ii) terbinafine at 0.25 μg/ml plus ketoconazole at 16 μg/ml, (iii) terbinafine at 1 μg/ml and ketoconazole at 0.25 μg/ml, and (iv) terbinafine at 4 μg/ml and ketoconazole at 0.25 μg/ml, all showed fungicidal effect with the time required for fungicidal effect to be shown decreasing as the terbinafine concentrations increased.

Comparison of combination effect of terbinafine (1 μg/ml) plus ketoconazole (0.25 μg/ml) with effect of each component alone at the same concentration of each and with a control is seen in FIG. 1C.

TABLE IV

| | | Stationery Test Inoculum $1.1 \times 10^5$ cfu/ml cfu/ml[a] | | | | | |
|---|---|---|---|---|---|---|---|
| | mg/ml | 0 hrs | 6 hrs | 24 hrs | 48 hrs | 72 hrs | 96 hrs |
| Control | $0^b$ | $1.1 \times 10^5$ | $1.8 \times 10^6$ | $1.7 \times 10^7$ | $2.0 \times 10^7$ | $3.0 \times 10^7$ | $2.9 \times 10^7$ |
| Turbinafine (T) | 0.25 | $1.1 \times 10^5$ | $4.6 \times 10^5$ | $8.4 \times 10^6$ | $1.3 \times 10^7$ | $1.6 \times 10^7$ | $1.5 \times 10^7$ |
| | 1.0 | $1.1 \times 10^5$ | $2.2 \times 10^5$ | $2.9 \times 10^6$ | $4.6 \times 10^6$ | $8.0 \times 10^6$ | $4.7 \times 10^6$ |
| | 4.0 | $1.1 \times 10^5$ | $3.2 \times 10^5$ | $5.2 \times 10^4$ | $1.2 \times 10^6$ | $1.3 \times 10^6$ | $2.5 \times 10^6$ |
| | 16.0 | $1.1 \times 10^5$ | $1.8 \times 10^5$ | $4.0 \times 10^4$ | $2.8 \times 10^4$ | $1.2 \times 10^5$ | $1.0 \times 10^4$ |
| | 64.0 | $1.1 \times 10^5$ | $2.2 \times 10^5$ | $6.7 \times 10^4$ | $3.4 \times 10^4$ | $1.7 \times 10^5$ | $9.8 \times 10^4$ |
| Ketoconazole | 0.25 | $1.1 \times 10^5$ | $7.0 \times 10^5$ | $1.4 \times 10^6$ | $1.4 \times 10^6$ | $1.9 \times 10^6$ | $1.5 \times 10^6$ |
| | 1.0 | $1.1 \times 10^5$ | $5.0 \times 10^5$ | $1.3 \times 10^6$ | $1.6 \times 10^6$ | $1.9 \times 10^6$ | $1.1 \times 10^6$ |
| | 4.0 | $1.1 \times 10^5$ | $4.8 \times 10^5$ | $9.1 \times 10^5$ | $1.2 \times 10^6$ | $1.3 \times 10^6$ | $7.7 \times 10^5$ |
| | 16.0 | $1.1 \times 10^5$ | $3.8 \times 10^5$ | $4.4 \times 10^5$ | $4.8 \times 10^5$ | $5.4 \times 10^5$ | $6.5 \times 10^5$ |
| | 64.0 | $1.1 \times 10^5$ | $1.7 \times 10^5$ | $3.2 \times 10^4$ | $7.2 \times 10^1$ | $4^c$ | $4^c$ |
| (T) 0.062 + (K) | 4.0 | $1.1 \times 10^5$ | $2.1 \times 10^5$ | $3.4 \times 10^5$ | $2.0 \times 10^5$ | $1.3 \times 10^5$ | $4.8 \times 10^4$ |
| (T) 0.062 + (K) | 16.0 | $1.1 \times 10^5$ | $2.4 \times 10^5$ | $9.6 \times 10^4$ | $1.2 \times 10^4$ | $6.4 \times 10^2$ | $4^c$ |
| (T) 0.25 + (K) | 4.0 | $1.1 \times 10^5$ | $3.1 \times 10^5$ | $1.6 \times 10^4$ | $3.8 \times 10^3$ | $6.8 \times 10^3$ | $8.2 \times 10^1$ |
| (T) 0.25 + (K) | 16.0 | $1.1 \times 10^5$ | $1.8 \times 10^5$ | $4.2 \times 10^3$ | $6.1 \times 10^1$ | $4^c$ | $4^c$ |
| (T) 1.0 + (K) | 0.25 | $1.1 \times 10^5$ | $1.3 \times 10^5$ | $8.8 \times 10^1$ | $<4^c$ | $<4^c$ | $<4^c$ |
| (T) 1.0 + (K) | 1.0 | $1.1 \times 10^5$ | $3.0 \times 10^5$ | $1.2 \times 10^1$ | $<4^c$ | $<4^c$ | $<4^c$ |
| (T) 1.0 + (K) | 4.0 | $1.1 \times 10^5$ | $1.5 \times 10^5$ | 8 | 9 | $<4^c$ | $<4^c$ |
| (T) 1.0 + (K) | 16.0 | $1.1 \times 10^5$ | $1.3 \times 10^5$ | $1.2 \times 10^1$ | $<4^c$ | $<4^c$ | $<4^c$ |
| (T) 4.0 + (K) | 0.25 | $1.1 \times 10^5$ | $1.3 \times 10^5$ | 4 | $<4^c$ | $<4^c$ | $<4^c$ |

[a]Determined after dilution with saline and plating on Sabouraud's dextrose agar.
[b]Control tube and all drug-culture tubes contained a final concentration of 1% DMF, the solvent for the test agents.
[c]<4 cfu/ml = lower limit of the assay.

KETOCONAZOLE AND NAFTIFINE

In operations carried out in a manner similar to that described in Example I, naftifine and ketoconazole solutions in dimethylsulfoxide were separately prepared, diluted and employed to prepare drug-agar plates. The drug agar plates were then inoculated with cultures of fungi, incubated at 28° C. for 48 hours and the MIC recorded.

The FIC indexes were then calculated. The results are seen in Table V.

B. Fungicidal Effect

Naftifine and ketoconazole were tested alone and in combination against a strain of Candida albicans using broth dilution method and plating procedures to determine the number of colony forming units at appropriate intervals.

Naftifine and ketoconazole solutions were prepared as described in Part A except that dimethylformamide (DMF) was used as the initial solvent and 10 percent DMF in water was the vehicle for subsequent dilutions.

Drug culture tubes were prepared by combining one part single drug or mixed drug solution with nine parts of broth (Kimmig's medium) previously seeded with *C. albicans* MY1013. Each tube including culture control tubes contained 1 percent DMF. The yeast culture employed for seeding was that restored from Sabouraud's dextrose agar slant and grown in broth for 24 hours as described in Part A. The 24 hour culture was diluted 1:100 with 85 percent saline followed by a 1:100 dilution with Kimmig's medium to obtain concentration of colony forming units in the drug-culture tubes of about $10^4$ cfu/ml.

TABLE V

| | Minimum Inhibitory Concentration mg/ml | | | |
|---|---|---|---|---|
| Fungal Organism | Naftifine (N) | Ketoconazole (K) | Combination (N:K)* | FIC Index |
| *Candida albicans* MY1055+ | >128.0 | 64.0 | 64:0.25, 32:0.25, 16:0.25, 8:0.25, 4:4 | 0.04–0.25 or less (5)** |
| *C. albicans* MY992 | >128.0 | 2.0 | 64:1 | 0.75 or less |
| *C. albicans* MY1013 | 128.0 | 32.0 | 32:0.25, 16:0.25, 8:0.25, 4:0.25 | 0.04–0.26 (4) |
| *C. albicans* MY1029 | >128.0 | 64.0 | 64:0.25, 32:0.25, 16:0.25, 8:0.25, 4:8 | 0.04–0.25 or less (5) |
| *C. albicans* MY1058 | >128.0 | 0.25 | 64:0.25 | 1.25 or less |
| *C. tropicalis* MY1101 | >128.0 | 64.0 | 64:1, 32:1, 16:1, 8:2, 4:8 | 0.06–0.4 or less (5) |
| *C. tropicalis* MY1102 | 8.0 | 32.0 | 4:16 | 1.0 |
| *C. guilliermondie* MY1019 | 128.0 | 1.0 | 32:0.25, 16:0.25 | 0.38–0.5 (2) |
| *Cryptococcus neoformans* MY1046 | 64.0 | 2.0 | 16:0.125, 8:0.25, 4:0.5 | 0.25–0.31 (3) |
| *Cr. neoformans* MY1051 | 16.0 | 0.5 | 4:0.125 | 0.5 (1) |
| *Cr. neoformans* MY1050 | 16.0 | 2.0 | 4:1 | 0.75 |
| *Torulopsis glabrata* MY1059 | >128.0 | 8.0 | 64:2, 32:2, 16:2 | 0.31–0.5 or less (3) |
| *Saccharomyces cerevisiae* MY1027 | >128.0 | 2.0 | 64:0.25, 32:0.25, 16:0.5 | 0.25–0.38 or less (3) |

*The minimum inhibitory concentration of the combination (naftifine:ketoconazole) giving a FIC index of the number indicated under "FIC Index" or less
**Number of combinations indicated by number in parenthesis
+Internal identification of strain of organism The inoculated tubes were incubated at 35° C. without shaking, and aliquots were removed at 6, 24, 48, 72 and 96 hours and diluted with saline and plated in Sabouraud's dextrose agar. The plates were incubated at 35° C. for at least 48 hours, then the colonies counted and the number of cfu/ml in the undiluted drug-culture tubes calculated from the counts obtained. Representative data from this study is shown in FIG. 2. The number of cfu/ml in the culture control tube before incubation (0 hour) was determined to be $1.2 \times 10^4$, after 24 hours of incubation $9.0 \times 10^6$, and by 48 hours $3.0 \times 10^7$ indicating substantially maximum growth had been obtained under these conditions. The lowest concentrations of naftifine (N) (16 μg/ml) and ketoconazole (K) (2 μg/ml) are also shown alone and in combination. The cfu/ml for naftifine are $3.2 \times 10^4$, $2.3 \times 10^6$, $1.4 \times 10^7$, $1.9 \times 10^7$, and $3.1 \times 10^7$ cfu/ml for 6, 24, 48, 72 and 96 hours, cfu/ml (24 hours), cfu/ml (48 hours), cfu/ml (72 hours) and cfu/ml (96 hours). The cfu/ml for ketoconazole for these times are respectively, $3.8 \times 10^4$, $4.6 \times 10^4$, $9.9 \times 10^4$, $1.9 \times 10^5$, $2.2 \times 10^5$ cfu/ml. The cfu/ml for the combination is $1.2 \times 10^4$ cfu/ml at 6 hours and 0 from and after 24 hours. The figure shows that naftifine alone was only slightly fungistatic for 24 hours and that by 48 hours substantially full growth of the culture had occurred. Ketoconazole when employed alone was fungistatic with <1.5 log increase over the 96 hour test period. The combination, however, produced a fungicidal effect by 24 hours.

The success of the combination depends on the susceptibility of the organism to the squalene oxidase inhibitor, i.e., to naftifine or to terbinafine. If the organism is susceptible to the latter, combination thereof with the conazole compound will produce both a synergistic and fungicidal effect. The optimum concentrations for achieving the latter effects may vary not only with the organism but with a particular strain.

From the foregoing test results and from known dosage ranges of the "conazole compound" (14α-methyl demethylase inhibitor) and the "allylamine compound" (squalene epoxidase inhibitor) as applied to man, it is determined that generally from about 2.85 to about 4.75 mg/kg of body weight of the conazole compound and about 2.8 to about 4.75 mg/kg of body weight of the allylamine compound is to be employed while considering patient's health, weight, age and other factors which influence response to a drug as well as the particular drug to be employed. These amounts when expressed as doses suitable for man are in the range of from about 200 to about 400 mg of each active ingredient given BID by oral or parenteral route.

According to the present invention, the synergistic antifungal or fungicidal composition may be formulated for injection and may be presented in unit dosage form in ampoules or in multidose containers, if necessary with an added preservative. The compositions may also take such forms as suspensions, solutions or emulsions in oily or aqueous vehicles, and may contain formulating agents such as suspending, stabilizing and/or dispersing agents. Alternatively, the active ingredients may be in powder form for reconstituting with a suitable vehicle prior to parenteral or oral administration.

The compounds also may be prepared in tablet or capsule form as well as in liquid form for oral administration. These also may be in unit dosage form.

For parenteral applications the drugs may be formulated in conventional parenteral solutions such as 0.85 percent sodium chloride or 5 percent dextrose in water, or other pharmaceutically acceptable compositions.

The outstanding properties are most effectively utilized when the conazole compound and the allylamine compound are formulated into novel pharmaceutical compositions with a pharmaceutically acceptable carrier according to conventional pharmaceutical compounding techniques.

In preparing the compositions in oral dosage form, the component drugs are intimately admixed with any of the usual pharmaceutical media, including for liquid preparations, liquid carriers such as water, glycols, oils, alcohols, and the like, and for solid preparations such as capsules and tablets, solid carriers such as starches, sugars, kaolin, ethyl cellulose, generally with lubricant such as calcium stearate, together with binders, disintegrating agents and the like. Because of their ease in administration, tablets and capsules represent the most advantageous oral dosage form. It is especially advantageous to formulate the compositions in unit dosage form for ease of administration and uniformity of dosage. Compositions in unit dosage form constitutes an aspect of the present invention.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 200 to 400 milligrams of each of the component drugs.

The following examples illustrate novel compositions but are not to be construed as limiting:

EXAMPLE I 1000 compressed tablets each containing 200 milligrams of ketoconazole and 300 milligrams of naftifine are prepared from the following formulation:

|  | Grams |
| --- | --- |
| Ketoconazole | 200 |
| Naftifine | 300 |
| Starch | 750 |
| Dibasic calcium phosphate hydrous | 5000 |
| Calcium stearate | 2.5 |

The finely powdered ingredients are mixed well and granulated with 10 percent starch paste. The granulation is dried and compressed into tablets.

EXAMPLE II 1000 hard gelatin capsules, each containing 210 milligrams of ketoconazole and 290 milligrams of terbinafine are prepared from the following formulation:

|  | Grams |
| --- | --- |
| Ketoconazole | 210 |
| Terbinafine | 290 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE III 250 milliliters of an injectable solution are prepared by conventional procedures having the following formulation:

| Dextrose | 12.5 grams |
| --- | --- |
| Water | 250 milliliters |
| Ketoconazole | 200 milligrams |
| Terbinafineium | 200 milligrams |

The ingredients are blended and thereafter sterilized for use.

What is claimed is:

1. A method for treating subjects with mycotic infecions comprising directing to the site where control is desired by administering a fungicidally effective amount of:
    (1) a compound having 14α-methyldemethylase inhibitor activity and named cis-1-acetyl-4-[4-[[2-(2,4-dichlorophenyl)-2-(1H-imidazol-1-ylmethyl)-1,3-dioxolan-4-yl]-methoxy]phenyl]piperazine(-ketoconazole); and
    (2) a compound having squalene epoxidase inhibitor activity and named N-methyl-N-(3-phenyl-propenyl)-1-naphthalenemethamine hydrochloride (naftifine);

wherein the compound having 14α-methyldemethylase inhibitor activity is employed in an amount of from about 2.85 to 4.75 mg/kg of body weight, and wherein the compound having squalene epoxidase inhibitor activity is employed in an amount of from about 2.85 to 4.75 mg/kg of body weight.

2. A method according to claim 1 wherein the treatment is by parenteral administration.

3. A method according to claim 1 wherein the treatment is by oral administration.

4. An oral pharmaceutical composition suitable for treating mycotic infections in unit dosage form comprising per dosage unit of:
    (1) from about 200 to 400 milligrams of a compound having 14α-methyldemethylase inhibitor activity and named cis-1-acetyl-4-[4-[[2-(2,4-dichlorophenyl)-2-(1H-imidazole-1-ylmethyl)-1,3-dioxolan-4-yl]-methoxy]-phenyl]piperazine (ketoconazole); and
    (2) from about 200 to 400 milligrams of a compound having squalene epoxidase inhibitor activity and named N-methyl-N-(3-phenylpropenyl-1-naphthalenemethamine hydrochloride (naftifine);

wherein said compounds are in admixture with a pharmaceutically acceptable carrier.

5. A composition according to claim 4 in which the unit dosage form is a tablet.

6. A composition according to claim 4 in which the unit dosage form is a capsule.

7. A parenteral pharmaceutical composition suitable for treating mycotic infection in unit dosage form: comprising per dosage unit of:
    from about 200 to 400 milligrams of a compound having 14α-methyldemethylase inhibitor activity and named cis-1-acetyl-4-[4-[[2-(2,4-dichlorophenyl)-2-(1H-imidazol-ylmethyl)-1,3-dioxolan-4-yl]-methoxyphenyl]piperazine (ketoconazole); and from about 200 to 400 milligrams of a compound having squalene epoxidase inhibitor activity and named N-methyl-N-(3-phenylpropenyl)-1-naphthalenemethamine hydrochloride (naftifine);

wherein said compounds are in admixture in aqueous parenteral compositions.

* * * * *